United States Patent
Pragt et al.

(10) Patent No.: US 9,187,400 B2
(45) Date of Patent: Nov. 17, 2015

(54) PROCESS FOR SEPARATING MONOCHLOROACETIC ACID AND DICHLOROACETIC ACID VIA EXTRACTIVE DISTILLATION USING AN ORGANIC SOLVENT

(71) Applicant: AKZO NOBEL CHEMICALS INTERNATIONAL B.V., Amersfoort (NL)

(72) Inventors: Johannes Jozef Pragt, Dieren (NL); Mark Theodorus Gerardus Jongmans, Deventer (NL); Gerrald Bargeman, Wageningen (NL); Boelo Schuur, Enschede (NL); Jacobus Theodorus Josef Aaldering, Doesburg (NL); Melle Rinze Nieuwhof, Dieren (NL); Anton Alexandru Kiss, Arnhem (NL); André Banier De Haan, Best (NL); Alex Londoño Rodriguez, Maastricht (NL); Cornelis Johannes Govardus Van Strien, Elst (NL)

(73) Assignee: AKZO NOBEL CHEMICALS INTERNATIONAL B.V., Amersfoort (NL)

( * ) Notice: Subject to any disclaimer, the term of this patent is extended or adjusted under 35 U.S.C. 154(b) by 0 days.

(21) Appl. No.: 14/390,244

(22) PCT Filed: Apr. 3, 2013

(86) PCT No.: PCT/EP2013/056969
§ 371 (c)(1),
(2) Date: Oct. 2, 2014

(87) PCT Pub. No.: WO2013/150042
PCT Pub. Date: Oct. 10, 2013

(65) Prior Publication Data
US 2015/0112097 A1 Apr. 23, 2015

Related U.S. Application Data

(60) Provisional application No. 61/621,134, filed on Apr. 6, 2012.

(30) Foreign Application Priority Data

Apr. 6, 2012 (EP) .................................... 12002517

(51) Int. Cl.
C07C 51/44 (2006.01)
C07C 51/46 (2006.01)

(52) U.S. Cl.
CPC ................. *C07C 51/44* (2013.01); *C07C 51/46* (2013.01)

(58) Field of Classification Search
CPC ............................... C07C 51/44; C07C 53/16
See application file for complete search history.

(56) References Cited

U.S. PATENT DOCUMENTS 1,921,717 A * 8/1933 Amstutz ...................... 562/603
3,772,157 A 11/1973 Horsley

FOREIGN PATENT DOCUMENTS

| DE | 23 47 998 | | 4/1945 |
|---|---|---|---|
| DE | 39 04 590 | | 8/1990 |
| DE | 3904590 | A1 * | 8/1990 |
| EP | 0 557 169 | | 8/1993 |
| JP | 47-29886 | B | 8/1972 |
| JP | 47-30165 | B | 8/1972 |

OTHER PUBLICATIONS

Dejanovic, I. et al., "Dividing wall column—A breakthrough towards sustainable distilling", Chemical Engineering and Processing, 2010, vol. 49, pp. 559-580.
Freund, H. et al., "Process Intensification, 4. Plant Level", Ullman's Encyclopedia of Industrial Chemistry, as published online Jul. 15, 2011.
Laurence, C. et al., Lewis Basicity and Affinity Scales, Data and Measurement, 2010, Chapter 3—The BF3 Affinity Scale.
Laurence, C. et al., Lewis Basicity and Affinity Scales, Data and Measurement, 2010, Chapter 7—The Measurement of Lewis Basicity and Affinity in the Laboratory.
Murrieta-Duenas, R. et al., Analysis of control properties of intensified distillation sequences: Reactive and extractive cases, Chemical Engineering Research and Design, 2011, vol. 89, pp. 2215-2227.
Richardson, J. et al., "Particle Technology and Separation Processes", Coulson and Richardson's Chemical Engineering, 2002, vol. 2, Fifth Edition, pp. 612-629.
International Search Report for Application No. PCT/EP2013/056969, mailed on Jun. 28, 2013.
European Search Report for EP Application No. 12002517.6, dated Oct. 2, 2012.

* cited by examiner

*Primary Examiner* — Sudhakar Katakam
(74) *Attorney, Agent, or Firm* — Kenyon & Kenyon LLP

(57) ABSTRACT

The present invention pertains to a process for separating monochloroacetic acid and dichloroacetic acid from one another via extractive distillation using (a) an extractive agent that is chemically stable and has a $BF_3$ affinity of between 65 kJ/mole and 110 kJ/mole and (b) an organic solvent that is either an acid with a lowest pKa of between 3.0 and 6.5 or a base with a $BF_3$ affinity of between 40 kJ/mole and 75 kJ/mole with the proviso that said $BF_3$ affinity is lower than the $BF_3$ affinity of the extractive agent, said organic solvent being chemically stable, and having a boiling point at atmospheric pressure of at least 468K, comprising the steps of (i) contacting a mixture comprising monochloroacetic acid and dichloroacetic acid with the extractive agent, (ii) distilling the mixture obtained in step (i) to obtain a monochloroacetic acid stream and a stream comprising dichloroacetic acid and the extractive agent, (iii) subjecting the stream comprising dichloroacetic acid and the extractive agent to a regeneration step, wherein the organic solvent is contacted with the mixture comprising monochloroacetic acid and dichloroacetic acid of step (i), or wherein the organic solvent is contacted with the mixture obtained in step (i) prior to and/or during step (ii), or wherein the organic solvent is contacted with the stream comprising dichloroacetic acid and the extractive agent obtained in step (ii) prior to or during step (iii), or any combination thereof.

20 Claims, No Drawings

PROCESS FOR SEPARATING MONOCHLOROACETIC ACID AND DICHLOROACETIC ACID VIA EXTRACTIVE DISTILLATION USING AN ORGANIC SOLVENT

REFERENCE TO RELATED APPLICATIONS

This application is the U.S. National Phase of PCT/EP2013/056969, filed on Apr. 3, 2013, and claims the benefit of EP Application No. 12002517.6, filed on Apr. 6, 2012, and U.S. Provisional Application No. 61/621,134, filed on Apr. 6, 2012.

The present invention relates to a process for separating monochloroacetic acid and dichloroacetic acid from one another via extractive distillation.

The predominant industrial route for the production of monochloroacetic acid is by reacting acetic acid with chlorine. Such a process is commonly known and generally makes use of a reactor in which a mixture of liquid acetic acid (HAc) is reacted with chlorine under anhydrous conditions, in the presence of a catalyst. In the reactor, monochloroacetic acid (MCA) and gaseous HCl are formed together with by-products of which dichloroacetic acid (DCA) and trichloroacetic acid (TCA) are examples.

After chlorination, DCA is present in a significant amount in the MCA-containing reaction product mixture, typically about 3-10 wt %. To reduce the amount of DCA in the MCA, the MCA/DCA-containing product mixture should be subjected to a purification process. Known purification methods include (melt) crystallization and reduction of the DCA with hydrogen in the presence of a hydrogenation catalyst. These methods can be applied on MCA/DCA streams which have already been purified but still comprise a low amount of DCA, but also on streams which comprise a considerably higher amount of DCA (DCA concentrations typically in the range of between 50 ppm and 70 wt %).

With melt crystallization, the concentration of DCA in a crude MCA feed can only be reduced with a one-stage recrystallization by a factor of approximately 4, i.e., for example, from 3 to 0.7-0.8 wt %. Hence, for the production of pure MCA, the melt crystallization is repeated several times. After several crystallizations, a mother liquor remains comprising a mixture of MCA and DCA. Although this mother liquor still comprises at least 30 wt % MCA, depending on the cooling conditions, it cannot be converted into a sellable product by further crystallization. Hence, there is a need for an economically feasible method for separating MCA and DCA from one another so that said mother liquor does not have to be discarded, and which may even make the melt crystallization process redundant.

As the boiling points of MCA and DCA are very close (462 K and 467 K, respectively), they cannot easily be separated from one another by simple distillation because the volatility of the two components is nearly the same (i.e. relative volatility about 1), causing them to evaporate at nearly the same temperature at a similar rate, making normal distillation impractical. However, it is known that components in a mixture having a relative volatility value close to 1 may be separated via extractive distillation. Extractive distillation is a distillation in the presence of a third component (hereinafter denoted as extractive agent or EA) that interacts differently with the components of the mixture, thereby causing their relative volatility to change. This enables the new three-part mixture to be separated by normal distillation. The essence of extractive distillation is for instance explained by J. F. Richardson, J. H. Harker, and J. R. Backhurst, in *Coulson and Richardson's Chemical Engineering*, Vol. 2, 5$^{th}$ edition (2002), Butterworth-Heinemann, pages 617-619, and by Hannsjörg Freund and Kai Sundmacher, in "Process Intensification, 4. Plant Level" (published Online: 15 Jul. 2011), page 22, in Ullman's Encyclopedia of Industrial Chemistry: *Extractive Distillation [187-190]*.

A method for separating MCA and DCA from each other by extractive distillation is known from JP 47-30165. It describes the use of sulfuric acid as extractant. Addition of sulfuric acid to a mixture comprising MCA and DCA results in a higher volatility difference. Upon distillation, DCA containing a small amount of MCA is distilled over the top, while the bottom product is a mixture of sulfuric acid and MCA containing a very small amount of DCA. The bottom product is subsequently distilled to yield MCA and sulfuric acid. A disadvantage of this method is, however, that the thus obtained MCA has to be subjected to a crystallization step for refining. Furthermore, traces of sulfuric acid that may end up in the DCA top product will lead to enhanced deactivation of the catalyst which is used in a subsequent hydrogenation step for conversion of DCA to MCA.

JP 47-29886 discloses a similar process wherein sulfolane is used as the extractive agent. It is true that the use of sulfolane as extractive agent has the advantage that the extractive agent can be recovered and reused relatively easily. However, also in this case, the degree of separation of monochloroacetic acid from dichloroacetic acid leaves room for improvement, since the achieved improvement in relative volatility of the MCA/DCA system is small.

It is therefore an objective of the present invention to provide a process for separating monochloroacetic acid and dichloroacetic acid from one another via extractive distillation that is economically feasible because good separation is achieved, while at the same time the used extractive agent can be regenerated relatively easily.

It has surprisingly been found that this objective is met if a specific extractive agent is used in combination with a specific organic solvent.

More specifically, the present invention relates to a process for separating monochloroacetic acid and dichloroacetic acid from one another via extractive distillation using (a) an extractive agent that is chemically stable and has a $BF_3$ affinity of between 65 kJ/mole and 110 kJ/mole and (b) an organic solvent that is either an acid of which the lowest pKa is between 3.0 and 6.5 or a base with a $BF_3$ affinity of between 40 kJ/mole and 75 kJ/mole with the proviso that said $BF_3$ affinity is lower than the $BF_3$ affinity of the extractive agent, said organic solvent being chemically stable, and having a boiling point at atmospheric pressure of at least 468 K, comprising the steps of
  (i) contacting a mixture comprising MCA and DCA with the extractive agent,
  (ii) distilling the mixture obtained in step (i) to obtain a MCA stream and a stream comprising DCA and the extractive agent,
  (iii) subjecting the stream comprising DCA and the extractive agent to a regeneration step,
wherein the organic solvent is contacted with the mixture comprising MCA and DCA of step (i), or wherein the organic solvent is contacted with the mixture obtained in step (i) prior to and/or during step (ii), or wherein the organic solvent is contacted with the stream comprising DCA and the extractive agent obtained in step (ii) prior to or during step (iii), or any combination thereof.

More particularly, step (i), i.e. the contacting of a mixture comprising MCA and DCA with an extractive agent, can take place inside the column which is used to perform the extractive distillation. However, it is also possible to contact the mixture comprising MCA and DCA with the extractive agent prior to their entrance into the column used for the extractive distillation (i.e. premixing the mixture comprising MCA and DCA with extractive agent and feeding the resulting mixture to the column in order to perform the extractive distillation). A combination of the two techniques is also possible. It is noted that it is preferred to contact the mixture comprising MCA and DCA with an extractive agent inside the extractive distillation column. In that case, preferably, the extractive agent is fed to said column at a stage above the stage at which the mixture comprising MCA and DCA is fed to said column, as in that case there will be an excess of extractive agent present higher up in the column to catch any traces of DCA.

Furthermore, there are several possibilities of introducing the organic solvent into the process. It is possible to contact the mixture comprising MCA and DCA of step (i) with said organic solvent. It is also possible to contact the organic solvent with the mixture obtained in step (i) prior to and/or during step (ii). Another option is to contact the organic solvent with the stream comprising DCA and the extractive agent obtained in step (ii) prior to or during step (iii). As the skilled person will understand, any combination of the just described options is also possible.

The extractive agent and the organic solvent used in the process according to the present invention are chemically stable. To evaluate the stability of these compounds the following test can be conducted. DCA and said compound (i.e. extractive agent or organic solvent) are added to a 10 mL vial in a 1/1 mole based ratio. The total amount of DCA and said compound supplied to the vial is 2 mL. The vial containing the mixture is stored at a temperature of 433 K for 24 hours. Subsequently, one droplet of the sample is added to 1.5 mL acetone. The mixture of the sample and the acetone is analyzed using GC-MS (Gas Chromatography-Mass Spectrometry) according to the following protocol:

Equipment: Shimadzu GC-17A Gas Chromatograph+Shimadzu GC MS-QP5000 Detector MS
Column: Chrompack VF-1 ms 25 m*0.25 mm ID DF=0.40 μm 100% dimethylpolysiloxane
GC method: Injection temperature: 573 K
  Interface temperature: 523 K
  Column inlet pressure: 24.5 kPa
  Column flow: 0.8 mL/min
  Linear velocity: 35.5 cm/sec
  Split ratio: 10
  Carrier: Helium
  Total flow: 9.4 mL/min
  Carrier flow: 9.4 mL/min
  Injection volume: 1 μL
  Start Temperature: 323 K
  Heating rate: 10 K/min
  End temperature: 563 K (9 minutes hold time)
MS settings: Start time: 1.4 min
  Stop time: 33 min
  Start m/z: 35 g/mole
  Stop m/z: 400 g/mole
  Scan speed: 2,000
  Interface temperature: 523 K
  Acetone cut time: 1.4 min
  Detector voltage: 1.3 kV
  Threshold: 1,000
  Interval: 0.2 seconds The ratio of the peak area of the impurity over extractive agent or organic solvent should be below 0.3, preferably below 0.1, and more preferably below 0.05 to consider the extractive agent or organic solvent as chemically stable.

These peak areas can be converted using conventional calibration techniques the skilled person is familiar with into percentages of degenerated extractive agent or organic solvent, based on the initial total amount of extractive agent or organic solvent used. Accordingly, the term "chemically stable" as used throughout the specification for the extractive agent and the organic solvent denotes that less than 45% of extractive agent, resp. organic solvent (relative on a mole basis) will be degenerated when kept for 24 hours at 433 K in the presence of DCA in a 1/1 mole ratio. Preferably, it denotes that less than 15% of extractive agent, resp. organic solvent (relative on a mole basis) will be degenerated when kept for 24 hours at 433 K in the presence of DCA in a 1/1 mole ratio. Most preferably, it denotes that less than 7.5% of extractive agent, resp. organic solvent (relative on a mole basis) will be degenerated when kept for 24 hours at 433 K in the presence of DCA in a 1/1 mole ratio.

The term "extractive agent" as used throughout this specification is meant to denote any additive which forms a stronger complex with DCA than with MCA. By definition, the extractive agent is less volatile than the components to be separated.

The $BF_3$ affinity of an extractive agent can be determined according to the test method which is described in Christian Laurence and Jean-Francois Gal, *Lewis Basicity* and Affinity Scales, Data and Measurement, 2010, John Wiley & Sons Ltd, ISBN 978-0-470-74957-9, Chapters 3 and 7. A short description of said test method will be provided below.

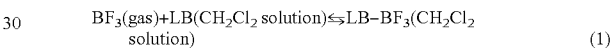

$$BF_3(gas)+LB(CH_2Cl_2 \text{ solution}) \leftrightarrows LB-BF_3(CH_2Cl_2 \text{ solution}) \quad (1)$$

(with LB being Lewis Base, i.e. the extractive agent)

Heat evolved in complexation reaction (1) is measured in a heat-flux microcalorimeter thermoregulated at 298 K. The measuring cell contains ~3 $cm^3$ of a dilute solution of Lewis base (i.e. extractive agent) in $CH_2Cl_2$. The base concentration depends on its strength: it usually ranges from 0.2 mole/L for strong bases to 1 mole/L for weak bases. Aliquots in the range (1-3) $10^{-4}$ mole of gaseous boron trifluoride ($BF_3$) are added to the solution of base by means of a vacuum line. Each addition of a quantity of $BF_3$ (n mole) generates a quantity of heat, Q. When the reaction is complete, the enthalpy of complexation for each addition, $\Delta H°$, is defined as the Q/n ratio. The method is equivalent to a discontinuous titration of the base by the acid $BF_3$. One titration provides 6-8 $\Delta H°$ values. Their mean and the corresponding confidence limits, usually at the 95% level, are calculated. The precision is fairly good (0.2-0.5% within a set, 0.5-1% between sets) and the accuracy is estimated as 1-2%.

It is noted that it is essential to use dry solvents and reactants because traces of humidity (and also other impurities) tend to induce an additional heat of reaction. Moreover, $BF_3$ releases hydrogen fluoride by slow hydrolysis, resulting in etching of the glass parts of the system (see also Chapter 7.1.2 of the above-mentioned book of Laurence and Gal). It is furthermore noted that the calorimeter can be calibrated by the Joule effect (see Chapter 7.1.3 of the above-mentioned book of Laurence and Gal).

The extractive agent is preferably selected from the group consisting of phosphine oxides, aldehydes, ketones, ethers, and amides which are chemically stable and have a $BF_3$ affinity of between 65 kJ/mole and 110 kJ/mole. More preferably, the extractive agent is selected from the group consisting of aldehydes, ketones, ethers, and amides which are chemically stable and have a $BF_3$ affinity of between 65 kJ/mole and 110 kJ/mole. Most preferably, the extractive agent is selected from the group consisting of ketones and ethers which are chemically stable and have a $BF_3$ affinity of between 65 kJ/mole and 110 kJ/mole.

As said, the extractive agent according to the present invention has a $BF_3$ affinity of at least 65 kJ/mole. Preferably, however, it has a $BF_3$ affinity of at least 70 kJ/mole and most preferably of at least 75 kJ/mole.

The extractive agent according to the present invention has a $BF_3$ affinity of at most 110 kJ/mole. Preferably, however, it has a $BF_3$ affinity of at most 100 kJ/mole, and most preferably, it has a $BF_3$ affinity of at most 90 kJ/mole.

In a particularly preferred embodiment, the extractive agent is selected from the group consisting of tetraglyme, diethylene glycol dibutyl ether, dihexyl ether, diethylene glycol dipentyl ether, and dihexyl ketone. The most preferred extractive agents are tetraglyme, diethylene glycol dibutyl ether, and dihexyl ether.

As mentioned earlier, the extractive agent improves the separation between MCA and DCA and can be regenerated relatively easily. However, the purity of several specific regenerated extractive agents can surprisingly be further improved by addition of an organic solvent with specific characteristics. This is especially important when the regenerated extractive agent is recycled to steps (i) and/or (ii). It is furthermore advantageous to recover higher amounts of relatively pure DCA, which reduces the amount of waste produced when the extractive agent is not reused. The presence of the specific organic solvent in the regeneration step increases the relative volatility between DCA and the extractive agent. This is especially important when the relative volatility between DCA and the extractive agent without the presence of the organic solvent becomes close to 1 during the regeneration and the extractive agent cannot be purified further in an economically viable way.

As described above, the organic solvent to be used in the process according to the present invention is an acid of which the lowest pKa—i.e. the pKa of the most acidic acid group—is between 3.0 and 6.5 or a base which has a $BF_3$ affinity of between 40 kJ/mole and 75 kJ/mole, with the proviso that said $BF_3$ affinity is lower than the $BF_3$ affinity of the extractive agent. Furthermore, said organic solvent is chemically stable (as defined above) and has a boiling point at atmospheric pressure of at least 468 K.

Preferably, the organic solvent has a boiling point at atmospheric pressure of at least 487 K, and more preferably of at least 517 K. Most preferably, the organic solvent is selected from the group consisting of diphenylether, nonanoic acid, neodecanoic acid, and dodecanoic acid.

As described above, in the process according to the present invention, a mixture comprising MCA and DCA is contacted with the extractive agent and optionally organic solvent according to the present invention. Besides MCA and DCA said mixture may furthermore comprise acetic acid. Said mixture preferably comprises at least 50 ppm of DCA, more preferably at least 500 ppm of DCA, and most preferably at least 5,000 ppm of DCA. Preferably, it comprises no more than 70 wt % of DCA, more preferably no more than 60 wt % of DCA, and most preferably no more than 50 wt % of DCA.

The extractive agent is preferably used in step (i) in such an amount that the ratio between extractive agent and DCA is at least 0.5, more preferably at least 1.0, and most preferably at least 2.5, all on a mole basis. For the sake of clarity, by the ratio between extractive agent and DCA is meant the total amount of extractive agent fed over the total amount of DCA fed to the extractive distillation column, both on a mole basis. The extractive agent is preferably used in such an amount that the ratio between extractive agent and DCA is at most 50, more preferably at most 30, even more preferably at most 20, and most preferably at most 10, all on a mole basis.

The organic solvent is preferably used in such an amount that the ratio between organic solvent and extractive agent is at least 0.1, more preferably at least 0.25, more preferably at least 0.5, even more preferably at least 0.75, and most preferably at least 0.9, all on a mole basis. For the sake of clarity, by the ratio between organic solvent and extractive agent is meant the total amount of organic solvent supplied to step (iii) over the total amount of extractive agent supplied to step (iii), both on a mole basis. The organic solvent is preferably used in such an amount that the ratio between organic solvent and extractive agent is at most 25, more preferably at most 15, more preferably at most 7.5, even more preferably at most 4, and most preferably at most 2, all on a mole basis.

The mixture comprising MCA, DCA, and extractive agent is distilled to obtain a MCA stream on the one hand and a stream comprising DCA and the extractive agent on the other. This extractive distillation step (step ii) is preferably performed at a pressure of below 500 mbar, more preferably below 250 mbar, and most preferably below 100 mbar.

The extractive distillation step is preferably performed with a temperature at the bottom of the distillation column of below 453 K, more preferably below 433 K, even more preferably below 413 K, and most preferably below 393 K.

In a next step, the extractive agent is regenerated by stripping or, preferably, by distillation of the stream comprising DCA and extractive agent. This step furthermore yields DCA. The regenerated extractive agent can be recycled to step (i) and/or step (ii) of the process according to the present invention.

In one embodiment, the regenerated extractive agent contains organic solvent and the mixture of extractive agent and organic solvent is recycled to step (i) and/or step (ii) of the process according to the present invention. In another embodiment, the extractive agent and the organic solvent are separated during or after step (iii) and the extractive agent and/or the organic solvent can then be recycled to steps (i), (ii), and/or (iii). It will be clear that this includes mixing with the stream comprising DCA between steps (ii) and (iii).

A skilled person will understand that the regeneration of DCA in step (iii), i.e. the separation of DCA and extractive agent, can be carried out in one, two, or more separation steps. Organic solvent can be introduced during any of these separation steps.

When the extractive agent and the organic solvent are separated after step (iii), techniques such as distillation can be used to separate the extractive agent from the organic solvent.

Step (iii) is preferably performed at a pressure of below 250 mbar, more preferably below 100 mbar, most preferably below 75 mbar.

In the case of a distillation step, the temperature at the bottom of the distillation column preferably is below 493 K, more preferably below 473 K, more preferably still below 453 K, and most preferably below 433 K.

A skilled person will understand that at identical pressures, the temperature at which the separation according to step (iii) of the present process is performed is higher than the temperature at which the extractive distillation of step (ii) is performed.

Suitable equipment which can be used to perform the extractive distillation step (step (ii)) according to the present invention includes conventional distillation columns comprising a reboiler and condenser. The regeneration step (step (iii)) can be performed in a conventional stripping column or a conventional distillation column, of which the latter is preferred.

In a preferred embodiment, step (ii) of the process according to the present invention is performed in combination with step (iii) in thermally coupled distillation columns or in a dividing wall column. Optionally, step (i) of the process according to the invention is integrated into the same thermally coupled distillation columns or dividing wall column. Thermally coupled distillation columns for example include a so-called Petlyuk configuration. It also includes, for example, an extractive distillation column which is thermally coupled with a side-rectifier or side-stripper. A set-up of thermally coupled distillation columns is conventionally known and for example described by R. Murrieta-Dueñas et al. in *Chemical Engineering Research and Design* 89, 2011, pp. 2215-2227. The Petlyuk setup and dividing wall column (DWC) are conventionally known and for instance described by I. Dejanović, Lj. Matijašević, and Ž. Olujić in *Chemical Engineering and Processing* 49, 2010, pp. 559-580. The use of thermally coupled distillation columns or a dividing wall column for carrying out both steps (ii) and (iii) (and optionally (i)) in the process of the present invention has the advantage that three fractions are produced: a first fraction comprising very pure MCA, a second fraction comprising very pure DCA and a third fraction comprising the extractive agent; the latter optionally also comprising the organic solvent. When the third fraction comprises both extractive agent and organic solvent, these compounds can optionally be further separated in a separate separation step.

In another preferred embodiment, step (iii) of the process according to the present invention is performed in thermally coupled distillation columns or in a dividing wall column. As already mentioned, thermally coupled distillation columns for example include a Petlyuk configuration. The use of thermally coupled distillation columns or a dividing wall column for carrying out step (iii) in the process of the present invention has the advantage that when DCA, extractive agent and organic solvent are fed to step (iii), three fractions are produced, a very pure DCA, a pure extractive agent, and a pure organic solvent.

The process according to the present invention can be used for further purification of streams comprising MCA and DCA which have already been purified, e.g. via a crystallization process, but still comprise a low amount of DCA. It is also suitable for the purification of crude streams which comprise a considerably higher amount of DCA.

The DCA obtained via the process according to the present invention can subsequently be subjected to a hydrogenation step by contacting it with hydrogen in the presence of a hydrogenation catalyst (such as for example disclosed in EP 557169) to produce MCA.

EXAMPLES

Comparative Example A

This example demonstrates the use of various extractive agents in the extractive distillation of a monochloroacetic acid (MCA)/dichloroacetic acid (DCA) feed. To determine the effect of the several extractive agents on the vapour-liquid equilibrium of the MCA/DCA mixture, an ebulliometer (Fischer VLE 602D) was used. In this ebulliometer the equilibrium vessel is a dynamic recirculating still, equipped with a Cottrel circulation pump. The heating capacity and the pressure were controlled using a control unit (Fischer system M101). The vapour condensation rate was kept constant at one drop per second. The condenser was operating at 343 K. The pressure was kept constant within a deviation of 0.02 kPa and the equilibrium temperature was measured with an uncertainty of 0.1 K. Equilibrium was reached after approximately 30-45 minutes, when the vapour temperature and the distillation rate were both constant. Samples of 30 µL from both the vapour and the liquid phase were taken with a 500 µL syringe.

For the experiments with the extractive agents sulfolane, tetraglyme, succinonitrile, tri-n-butylphosphate, tri-n-hexylamine, and diethylene glycol dibutyl ether, these samples were diluted with 0.75 mL of acetonitrile and 0.75 mL of water. The concentrations of the components were analyzed using high pressure liquid chromatography (HPLC, Varian Prostar). A silica-based Grace Prevail™ Organic Acid column (250 mm×4.6 mm) with a particle size of 5 µm was used. The temperature of the column was kept constant in an oven (Varian Prostar Model 510) at 313.2 K for all measurements. Detection of MCA and DCA was done using a UV detector (Varian Prostar Model 310) at 210 nm. The concentration of the extractive agent was calculated by means of a mass balance over the sample. The eluent flow was 1 mL/minute and consisted of 5 vol % acetonitrile and 95 vol % orthophosphoric acid solution (19 g/L) in Milli-Q water. The column was regenerated after each injection with pure acetonitrile. Each sample was injected twice. The mole fractions of the components in both the vapour and the liquid phase were obtained within an accuracy of 0.001 in mole fraction.

For the experiments with the extractive agent diethylene glycol dipentyl ether, dihexyl ketone, dihexyl ether and, tri-n-octylphosphine oxide, these samples were diluted with 1.5 mL of acetonitrile. The concentrations of the components were analyzed using high pressure liquid chromatography (HPLC, Varian Prostar). A silica-based Grace Prevail™ Organic Acid column (250 mm×4.6 mm) with a particle size of 5 µm was used. The temperature of the column was kept constant in an oven (Varian Prostar Model 510) at 313.2 K for all measurements. Detection of MCA and DCA was done using a UV detector (Varian Prostar Model 310) at 210 nm. The concentration of the extractive agent was calculated by means of a mass balance over the sample. The eluent flow was 1 mL/minute and consisted of 15 vol % acetonitrile and 85 vol % orthophosphoric acid solution (19 g/L) in Milli-Q water. The column was regenerated after each injection with pure acetonitrile. Each sample was injected twice. The mole fractions of the components in both the vapour and the liquid phase were obtained within an accuracy of 0.001 in mole fraction.

MCA (≥99.0%) and DCA (≥99.0%) used in this example were obtained from Sigma-Aldrich. Sulfolane (≥98%), tetraglyme (≥98.0%), succinonitrile (≥97.0%), tri-n-butylphosphate (≥99%), and tri-n-octylphosphine oxide (≥97.0%) were obtained from Fluka, and tri-n-hexylamine (≥96%), diethylene glycol dibutyl ether (≥99.0%), dihexyl ether (≥97.0%), and dihexyl ketone (≥97.0%) were obtained from Aldrich. Diethylene glycol dipentyl ether (≥99.0%) was obtained from Syncom. All chemicals were used without further purification. Before the experiment a solution of about 100 mL was prepared, in which the MCA/DCA ratio was 4/1 on a mole basis. Two EA/DCA ratios were utilized; 1/2 and 1/1, on a mole basis. All starting weights of the chemicals used for the vapour-liquid equilibrium experiments are shown in Table 1. The vapour-liquid equilibrium experiments were performed at 5, 7.5, and 10 kPa pressure. The relative volatility α presented in this example was calculated as follows:

$$\alpha = \alpha_{MCA/DCA} = (y_{MCA}/y_{DCA})/(x_{MCA}/x_{DCA})$$

where $y_{MCA}$ and $y_{DCA}$ are the weight fractions of MCA and DCA in the vapour phase, and $x_{MCA}$ and $x_{DCA}$ are the weight fractions of MCA and DCA in the liquid phase. The results of the vapour-liquid equilibrium experiments are listed in Table 2. From this Table, it follows that suitable extractive agents for improving the separation of MCA and DCA by extractive distillation are extractive agents having a $BF_3$ affinity (describing Lewis basicity) in excess of 65 kJ/mole (preferably in excess of 70 kJ/mole), since these extractive agents show a relative volatility in excess of 1.8 and several even in excess of 2.0 at a EA/DCA mole ratio of 1/1. This is higher than the relative volatility obtained with sulfolane.

TABLE 1

| EA (=Extractive Agent) | EA/DCA [mole base] | Mass MCA [g] | Mass DCA [g] | Mass EA [g] |
|---|---|---|---|---|
| EA free | — | 106.8 | 36.8 | — |
| Sulfolane | 1/1 | 83.5 | 28.5 | 26.5 |
|  | 1/2 | 93.2 | 31.8 | 14.8 |
| Succinonitrile | 1/1 | 86.0 | 29.3 | 18.2 |
|  | 1/2 | 94.8 | 32.3 | 10 |
| Tri-n-butyl-phosphate | 1/1 | 59.8 | 20.4 | 42.1 |
|  | 1/2 | 76.3 | 26 | 26.9 |
| Diethylene glycol dipentyl ether | 1/1 | 59.20 | 20.2 | 38.58 |
|  | 1/2 | 75.84 | 25.86 | 24.72 |
| Diethylene glycol dibutyl ether | 1/1 | 62.5 | 21.3 | 36.1 |
|  | 1/2 | 78.5 | 26.8 | 22.7 |
| Tetraglyme | 1/1 | 65.4 | 22.3 | 38.5 |
|  | 1/2 | 80.7 | 27.5 | 23.7 |
| Dihexyl ketone | 1/1 | 63.1 | 21.5 | 33.1 |
|  | 1/2 | 79.0 | 26.9 | 20.7 |
| Dihexyl ether | 1/1 | 63.7 | 21.7 | 31.4 |
|  | 1/2 | 80.0 | 27.3 | 19.6 |
| Tri-n-octyl-phosphine oxide | 1/1 | 47.4 | 16.1 | 46.1 |
|  | 1/2 | 65.4 | 21.7 | 30.8 |
| Tri-n-hexylamine | 1/1 | 54.3 | 18.5 | 38.7 |
|  | 1/2 | 71.7 | 24.4 | 25.6 |

Comparative Example B

To validate whether the extractive agents from Comparative Example A can be regenerated, vapour-liquid equilibrium experiments have been performed for the extractive agents in the presence of DCA. These regeneration experiments were performed with the same equipment, pressure conditions, analytical method, and extractive agents as in Comparative Example A.

Before the experiment a solution of 100 mL was prepared in which the EA/DCA mole ratio was 1/1. This is the expected composition from the extractive distillation column. For some of the extractive agents for which the regeneration was successful for the EA/DCA mole ratio of 1/1, regeneration experiments for the EA/DCA mole ratios of 5/1 and 9/1 have been performed as well. These high EA/DCA compositions are expected in the bottom of the regeneration column. All starting weights of the regeneration experiments are shown in Table 3.

The relative volatility α presented in this example was calculated as follows:

$$\alpha = \alpha_{DCA/EA} = (y_{DCA}/y_{EA})/(x_{DCA}/x_{EA})$$

where in this example $y_{DCA}$ and $y_{EA}$ are the weight fractions of DCA and EA in the vapour phase, and $x_{DCA}$ and $x_{EA}$ are the weight fractions of DCA and EA in the liquid phase.

The results of the vapour-liquid equilibrium experiments are listed in Table 4. Table 4 shows that the long chain ethers diethylene glycol dibutyl ether, diethylene glycol dipentyl ether, and tetraglyme can be regenerated. The same applies for dihexyl ether and dihexyl ketone. For tri-n-hexylamine, succinonitrile, tri-n-octylphosphine oxide, and tri-n-butylphosphate, the regeneration experiments were unsuccessful. For the extractive agents tri-n-hexylamine and tri-n-octylphosphine oxide, the complex formed with DCA was too strong and no vapour phase was formed in the ebulliometer (meaning that the extractive agent and DCA cannot be separated). Succinonitrile and tri-n-butylphosphate were both unstable in the strong acid environment (measured according to stability test mentioned in the description) and conse-

TABLE 2

| EA | $BF_3$ affinity [kJ/mole] | EA/DCA [mole base] | P = 5 kPa | | P = 7.5 kPa | | P = 10 kPa | |
|---|---|---|---|---|---|---|---|---|
|  |  |  | α [—] | T [K] | α [—] | T [K] | α [—] | T [K] |
| EA free | — | — | 1.3 | 380.9 | 1.3 | 389.9 | 1.3 | 397.0 |
| Sulfolane | 51 | 1/1 | 1.6 | 385.8 | 1.6 | 395.2 | 1.6 | 402.6 |
|  |  | 1/2 | 1.4 | 381.9 | 1.4 | 391.1 | 1.4 | 398.1 |
| Succinonitrile | 60 | 1/1 | 1.4 | 385.6 | 1.4 | 396.2 | 1.4 | 403.8 |
|  |  | 1/2 | 1.3 | 382.2 | 1.3 | 392.2 | 1.3 | 400.1 |
| Tri-n-butylphosphate | 85 | 1/1 | 2.2 | 386.0 | 2.2 | 395.5 | 2.2 | 402.9 |
|  |  | 1/2 | 1.8 | 382.2 | 1.7 | 391.5 | 1.7 | 398.5 |
| Diethylene glycol dipentyl ether | 79 | 1/1 | 2.3 | 388.8 | 2.2 | 398.1 | 2.1 | 405.0 |
|  |  | 1/2 | 1.8 | 384.8 | 1.8 | 394.0 | 1.7 | 400.8 |
| Diethylene glycol dibutyl ether | 79 | 1/1 | 2.3 | 387.4 | 2.2 | 396.6 | 2.2 | 403.6 |
|  |  | 1/2 | 1.8 | 383.6 | 1.8 | 392.8 | 1.7 | 399.8 |
| Tetraglyme | 84 | 1/1 | 2.4 | 391.6 | 2.3 | 400.9 | 2.3 | 408.1 |
|  |  | 1/2 | 1.9 | 385.3 | 1.9 | 394.4 | 1.8 | 401.6 |
| Dihexyl ketone | 73 | 1/1 | 1.8 | 391.3 | 1.8 | 397.6 | 1.8 | 403.2 |
|  |  | 1/2 | 1.6 | 388.4 | 1.6 | 395.4 | 1.6 | 401.2 |
| Dihexyl ether | 84 | 1/1 | 2.0 | 389.4 | 2.0 | 396.0 | 2.0 | 400.9 |
|  |  | 1/2 | 1.6 | 386.9 | 1.6 | 393.6 | 1.6 | 399.4 |
| Tri-n-octylphosphine oxide | 120 | 1/1 | 2.8 | 385.8 | 2.7 | 395.2 | 2.6 | 402.6 |
|  |  | 1/2 | 2.0 | 381.8 | 1.9 | 391.1 | 1.9 | 398.1 |
| Tri-n-hexylamine | 135 | 1/1 | 4.7 | 391.7 | 4.5 | 401.6 | 4.1 | 409.6 |
|  |  | 1/2 | 2.6 | 383.2 | 2.5 | 393.1 | 2.4 | 400.3 | quently did not fulfil the chemical stability criterion for suitable extractive agents. This comparative example shows that stability of the extractive agents in a strongly acidic environment is a prerequisite for the suitability of the extractive agent for this process.

Furthermore, it shows that for proper regeneration of the extractive agents, extractive agents with a $BF_3$ affinity (describing Lewis basicity) below 110 kJ/mole are needed, since these extractive agents show a relative volatility in excess of 2.0 during regeneration at an extractive agent/DCA mole ratio of 1/1. For the extractive agents with a $BF_3$ affinity between 65 k/mole and 110 kJ/mole, and preferably between 70 kJ/mole and 100 kJ/mole, good separation is obtained in both the extractive distillation (see Table 2 in Comparative Example A) and in the regeneration (see Table 4 in this comparative example). Table 4 furthermore shows that for several extractive agents, such as diethylene glycol dibutyl ether, tetraglyme, and dihexyl ether, relative volatilities drop from values in excess of 1 to values below 1 when the mole ratio of EA over DCA increases from 1 to 9. This means that the regenerated extractive agent obtained in this comparative experiment still contains significant amounts of DCA. This leaves room for improvement especially when the extractive agent is recycled to step (i).

TABLE 3

| EA | EA/DCA [mole ratio] | Mass DCA [g] | Mass EA [g] |
|---|---|---|---|
| Diethylene glycol dipentyl ether | 1/1 | 35.6 | 67.9 |
| | 9/1 | 5.0 | 85.1 |
| Diethylene glycol dibutyl ether | 1/1 | 65.3 | 38.2 |
| | 5/1 | 9.2 | 91.3 |
| | 9/1 | 5.8 | 83.7 |
| Tetraglyme | 1/1 | 40.9 | 72.3 |
| | 5/1 | 35.0 | 102 |
| | 9/1 | 6.1 | 95.9 |
| Dihexyl ketone | 1/1 | 50.1 | 77.1 |
| | 9/1 | 5.75 | 79.5 |
| Dihexyl ether | 1/1 | 40.6 | 58.7 |
| | 9/1 | 5.87 | 76.3 |
| Succinonitrile | 1/1 | 76.8 | 48.7 |
| Tri-n-butylphosphate | 1/1 | 74.3 | 35.4 |
| Tri-n-octylphosphine oxide | 1/1 | 70.3 | 23.8 |
| Tri-n-hexylamine | 1/1 | 64.5 | 30.3 |

Example 1

This example demonstrates the benefits of adding an organic solvent (S) to an extractive agent to improve the regeneration of the extractive agent (EA) in presence of DCA. As discussed below the experiments in this example have been performed with the same equipment and pressure conditions as used in Comparative Example A.

To determine the effect of an organic solvent on the vapor-liquid equilibrium of the DCA/EA mixture, an ebulliometer (Fischer VLE 602D) was used. In this ebulliometer the equilibrium vessel is a dynamic recirculating still, equipped with a Cottrel circulation pump. The heating capacity and pressure were controlled using a control unit (Fischer system M101). The vapor condensation rate was kept constant at one drop per second. The condenser was operating at 308 K. The pressure was maintained constant within a deviation of 0.02 kPa and the equilibrium temperature was measured with an uncertainty of 0.1 K. Equilibrium was typically reached after 30-45 minutes, when the vapor temperature and the distillation rate were both constant. Samples of about 50 μL from both vapor and liquid phase were taken with a 500 μL syringe. These samples were diluted with approximately 1 mL chloroform-d (i.e. deuterated chloroform) and transferred to 3 mm NMR-tubes. The concentrations of the components were analyzed using NMR spectroscopy (Bruker Avance DRX 600 NMR spectrometer) with a proton resonance frequency of 600 MHz, a carbon resonance frequency of 150 MHz, and a phosphorous resonance frequency of 243 MHz. The following standard $^1$H-NMR conditions were applied:

Probe: 5 mm BBO ATM probe and z-gradient feature
Operating temperature: 300 K
Operating frequency 600 MHz
Relaxation delay: 3 sec
Pulse: 30 degrees
Acquisition time: 2.65 sec
Power: 57 dB
Spectrum width: 12335 Hz
Number of scans: 128
Line broadening: 0.4 Hz
Integration $^1$H-NMR signals manually DCA (≥99%) used in this example was obtained from Sigma-Aldrich, nonanoic acid (>97%) was obtained from

TABLE 4

| EA | $BF_3$ affinity [kJ/mole] | EA/DCA [mole ratio] | P = 5 kPa | | P = 7.5 kPa | | P = 10 kPa | |
|---|---|---|---|---|---|---|---|---|
| | | | α [—] | T [K] | α [—] | T [K] | α [—] | T [K] |
| Tri-n-hexylamine | 135 | 1/1 | No vapor phase obtained, recovery EA not possible | | | | | |
| Tri-n-octylphosphine oxide | 120 | 1/1 | No vapor phase obtained, recovery EA not possible | | | | | |
| Diethylene glycol dipentyl ether | 79 | 1/1 | 11 | 428.2 | 10 | 438.4 | 12 | 445.8 |
| | | 9/1 | 2.4 | 448.3 | 2.6 | 459.1 | 2.7 | 467.2 |
| Diethylene glycol dibutyl ether | 79 | 1/1 | 2.4 | 422.5 | 2.4 | 432.3 | 2.0 | 439.5 |
| | | 5/1 | 0.80 | 427.9 | 0.84 | 438.1 | 0.90 | 445.7 |
| | | 9/1 | 0.71 | 429.2 | 0.76 | 439.5 | 0.81 | 447.0 |
| Tetraglyme | 84 | 1/1 | 2.3 | 443.4 | 2.2 | 452 | 2.0 | 458.3 |
| | | 5/1 | 0.76 | 446.7 | 0.80 | 457.2 | 0.84 | 464.7 |
| | | 9/1 | 0.68 | 448.6 | 0.70 | 458.7 | 0.73 | 466.1 |
| Dihexyl ketone | 73 | 1/1 | 15 | 411.1 | 12 | 420.2 | 11 | 427.0 |
| | | 9/1 | 2.6 | 431.0 | 2.7 | 441.4 | 2.6 | 448.8 |
| Dihexyl ether | 84 | 1/1 | 2.1 | 401.0 | 2.3 | 409.8 | 2.3 | 416.4 |
| | | 9/1 | 0.85 | 403.3 | 0.94 | 413.1 | 1.0 | 420.3 |

Sigma, diphenyl ether (>99%) and diethylene glycol dibutyl ether (99%) were obtained from Aldrich. All chemicals were used without further purification.

Before the experiment a solution of about 100 mL was prepared, in which the EA/DCA ratio was 9/1 on a mole basis, and the ENS ratio was 1/1 on a mole basis. Diethylene glycol dibutyl ether was used as extractive agent in this example. Nonanoic acid ($pK_a$=4.96) and diphenyl ether ($BF_3$ affinity in the range 40-65 kJ/mole) were used as organic solvents in different experiments. All starting weights of the chemicals used for the vapor-liquid equilibrium experiments are shown in Table 5. The vapor-liquid equilibrium experiments were performed at pressures of 5, 7.5, and 10 kPa. The relative volatilities α presented in this example were calculated as follows:

$$\alpha_{DCA/EA}=(y_{DCA}/y_{EA})/(x_{DCA}/x_{EA})$$

$$\alpha_{DCA/S}=(y_{DCA}/y_S)/(x_{DCA}/x_S)$$

where $y_{DCA}$, $y_{EA}$, and $y_S$ are the mole fractions of DCA, EA, and S in the vapor phase, and $x_{DCA}$, $x_{EA}$, and $x_S$ are the mole fractions of DCA, EA, and S in the liquid phase. The results of the vapor-liquid equilibrium experiments are listed in Table 6. The results presented in Table 6 clearly demonstrate that the addition of an organic solvent to the DCA/EA system facilitates easier regeneration of the extractive agent from DCA at an EA/DCA mole ratio of 9/1. The relative volatility of the DCA/extractive agent system ($\alpha_{DCA/EA}$) is above one in the presence of the organic solvent, contrary to the results presented in Comparative Example A for the extractive agent diethylene glycol dibutylether at an EA/DCA mole ratio of 9 (Table 2) where no organic solvent is added. This example therefore demonstrates the benefits of adding a weak base or weak acid as an organic solvent to an extractive agent according to the present invention when the extractive agent shows an azeotrope during regeneration from DCA. Moreover, the relative volatility of the DCA/S system ($\alpha_{DCA/S}$) is higher than one for both organic solvents, meaning that the regeneration of the extractive agent and the organic solvent from DCA is relatively easy.

TABLE 5

| EA | S | Mass DCA [g] | Mass EA [g] | Mass S [g] |
|---|---|---|---|---|
| Diethylene glycol dibutyl ether | Nonanoic acid | 3.3 | 50.7 | 36.7 |
| Diethylene glycol dibutylether | Diphenyl ether | 3.5 | 52.7 | 41.1 |

TABLE 6

| EA | S | P [kPa] | $\alpha_{DCA/EA}$ | $\alpha_{DCA/S}$ | T [K] |
|---|---|---|---|---|---|
| Diethylene glycol dibutyl ether | Nonanoic acid | 5 | 1.25 | 2.18 | 431.3 |
| | | 7.5 | 1.36 | 2.17 | 441.1 |
| | | 10 | 1.34 | 2.02 | 448.2 |
| Diethylene glycol dibutyl ether | Diphenyl ether | 5 | 1.49 | 1.27 | 426.5 |
| | | 7.5 | 1.56 | 1.31 | 436.7 |
| | | 10 | 1.81 | 1.56 | 444.4 |

Example 2

The organic solvents (S) added to the extractive agents (EA) to improve the extractive agent regeneration can affect the monochloroacetic acid (MCA)/dichloroacetic acid (DCA) separation in the extractive distillation column when the organic solvent is fed to the extractive distillation column or ends up in a stream which is recycled to the extractive distillation column. Therefore, this example presents the effects of the organic solvents added to the extractive agent on the relative volatility of the MCA/DCA system. As discussed below, the experiments in this example have been performed with the same equipment, pressure conditions and analytical method as used in Example 1. Only the temperature of the condenser of the ebulliometer was different. The temperature in this example was operated at 348 K to avoid MCA crystallization contrary to the regeneration experiments presented in Comparative Example B, where the condenser was operated at 308 K, since MCA was not present in the experiments described in Comparative Example B.

MCA (≥99%) and DCA (≥99%) used in this example were obtained from Sigma-Aldrich, nonanoic acid (≥97%) was obtained from Sigma, diphenyl ether (>99%) and diethylene glycol dibutyl ether (≥99%) were obtained from Aldrich. All chemicals were used without further purification.

Before the experiment a solution of about 100 mL was prepared, in which the MCA/DCA ratio was 4/1 on a mole basis, the EA/DCA ratio was 1/1 on a mole basis, and the ENS ratio was 1/1 on a mole basis. Diethylene glycol dibutyl ether was used as extractive agent in this example. Nonanoic acid and diphenyl ether were used as organic solvents in different experiments. All starting weights of the chemicals used for the vapor-liquid equilibrium experiments are shown in Table 7. The vapor-liquid equilibrium experiments were performed at pressures of 5, 7.5, and 10 kPa. The relative volatilities a presented in this example were calculated as follows:

$$\alpha_{MCA/DCA}=(y_{MCA}/y_{DCA})/(x_{MCA}/x_{DCA})$$

$$\alpha_{MCA/EA}=(y_{MCA}/y_{EA})/(x_{MCA}/x_{EA})$$

$$\alpha_{MCA/S}=(y_{MCA}/y_S)/(x_{MCA}/x_S)$$

where $y_{MCA}$, $y_{DCA}$, $y_{EA}$, and $y_S$ are the mole fractions of MCA, DCA, EA, and S in the vapor phase, and $x_{MCA}$, $x_{DCA}$, $x_{EA}$, and $x_S$ are the mole fractions of MCA, DCA, EA, and S in the liquid phase. The results of the vapor-liquid equilibrium experiments are listed in Table 8. The results displayed in Table 8 clearly show that the addition of the organic solvents to the extractive agent hardly influences the relative volatility of the MCA/DCA system at a DCA/EA mole ratio of 1. The relative volatilities for the MCA/DCA system presented in this example are almost identical to the organic solvent-free results presented in Table 2 for the extractant diethylene glycol dibutyl ether. Thus, this example demonstrates that the addition of an organic solvent (a weak acid or a weak base) to the extractive agent hardly affects the MCA/DCA separation in the extractive distillation column compared to adding only an extractive agent. Moreover, Table 8 shows that the relative volatilities of the MCA/EA system and MCA/S system are above one (and above the relative volatility of the MCA/DCA system as well) for both organic solvents/extractive agent mixtures and for all pressures, meaning that pure MCA can be obtained at the top of the extractive distillation column.

TABLE 7

| EA | S | Mass MCA [g] | Mass DCA [g] | Mass EA [g] | Mass S [g] |
|---|---|---|---|---|---|
| Diethylene glycol dibutyl ether | Nonanoic acid | 48.5 | 16.5 | 28.0 | 20.3 |
| Diethylene glycol dibutylether | Diphenyl ether | 49.5 | 16.9 | 28.6 | 22.3 |

TABLE 8

| EA | S | P [kPa] | $\alpha_{MCA/DCA}$ | $\alpha_{MCA/EA}$ | $\alpha_{MCA/S}$ | T [K] |
| --- | --- | --- | --- | --- | --- | --- |
| Diethylene glycol dibutyl ether | Nonanoic acid | 5 | 2.06 | 60.6 | 11.6 | 391.5 |
| | | 7.5 | 2.35 | 67.7 | 12.5 | 400.7 |
| | | 10 | 2.32 | 61.8 | 12.2 | 407.8 |
| Diethylene glycol dibutyl ether | Diphenyl ether | 5 | 2.27 | 99.5 | 3.4 | 389.6 |
| | | 7.5 | 2.33 | 91.1 | 3.7 | 399.0 |
| | | 10 | 2.29 | 90.2 | 3.7 | 405.8 |

The invention claimed is:

1. A process for separating monochloroacetic acid and dichloroacetic acid from one another via extractive distillation using (a) an extractive agent that is chemically stable and has a $BF_3$ affinity of between 65 kJ/mole and 110 kJ/mole and (b) an organic solvent that is either an acid of which the lowest pKa is between 3.0 and 6.5 or a base with a $BF_3$ affinity of between 40 kJ/mole and 75 kJ/mole with the proviso that said $BF_3$ affinity is lower than the $BF_3$ affinity of the extractive agent, said organic solvent being chemically stable, and having a boiling point at atmospheric pressure of at least 468 K, the process comprising the steps of
(i) contacting a mixture comprising monochloroacetic acid and dichloroacetic acid with the extractive agent,
(ii) distilling the mixture obtained in step (i) to obtain a monochloroacetic acid stream and a stream comprising dichloroacetic acid and the extractive agent,
(iii) subjecting the stream comprising dichloroacetic acid and the extractive agent to a regeneration step,
wherein the organic solvent is contacted with the mixture comprising monochloroacetic acid and dichloroacetic acid of step (i), or wherein the organic solvent is contacted with the mixture obtained in step (i) prior to and/or during step (ii), or wherein the organic solvent is contacted with the stream comprising dichloroacetic acid and the extractive agent obtained in step (ii) prior to or during step (iii), or any combination thereof.

2. The process according to claim 1 wherein the extractive agent is selected from the group consisting of phosphine oxides, aldehydes, ketones, ethers, and amides.

3. The process according to claim 1, wherein the organic solvent is selected from the group consisting of ketones, ethers, aldehydes, amides, and carboxylic acids.

4. The process according to claim 1, wherein the extractive agent has a $BF_3$ affinity of between 70 kJ/mole and 100 kJ/mole.

5. The process according to claim 1, wherein the mixture comprising monochloroacetic acid and dichloroacetic acid is contacted with the extractive agent and the organic solvent at least one of prior to or during step (ii).

6. The process according to claim 1, wherein the extractive agent is selected from the group consisting of tetraglyme, diethylene glycol dibutyl ether, and dihexyl ether.

7. The process according to claim 1, further comprising recycling the regenerated extractive agent to step (i) or step (ii).

8. The process according to claim 1, further comprising recycling the regenerated organic solvent to at least one of step (i), step (ii), or step (iii).

9. The process according to claim 1, wherein the organic solvent has a boiling point at atmospheric pressure of at least 517 K.

10. The process according to claim 1, wherein the organic solvent is selected from the group consisting of diphenylether, nonanoic acid, neodecanoic acid, and dodecanoic acid.

11. The process according to claim 1, wherein step (ii) is carried out in a distillation column, comprising a reboiler and condenser at a pressure below 500 mbar and with a temperature at the bottom of said distillation column being below 453 K.

12. The process according to claim 1, wherein in step (iii) the regeneration is performed by stripping or distillation of the stream comprising the dichloroacetic acid, the extractive agent, and the organic solvent.

13. The process according to claim 12 wherein step (iii) is carried out in a distillation column at a pressure below 250 mbar and with a temperature at the bottom of said distillation column being below 493 K.

14. The process according to claim 1, wherein the ratio between the extractive agent and the dichloroacetic acid in step (i) is between 0.5 and 50, on a mole basis.

15. The process according to claim 1, wherein the ratio between the total amount of the organic solvent supplied to step (iii) and the total amount of the extractive agent supplied to step (iii) is between 0.1 and 25, on a mole basis.

16. The process according to claim 1, wherein either
step (ii) and step (iii), and optionally step (i) or
step (iii)
are carried out in thermally coupled distillation columns or in a dividing wall column.

17. The process according to claim 1, wherein the dichloroacetic acid resulting from step (iii) is subsequently subjected to a hydrogenation step to produce monochloroacetic acid.

18. The process according to claim 2, wherein the organic solvent is selected from the group consisting of ketones, ethers, aldehydes, amides, and carboxylic acids.

19. The process according to claim 6, wherein the organic solvent is selected from the group consisting of diphenylether, nonanoic acid, neodecanoic acid, and dodecanoic acid.

20. The process according to claim 18, wherein step (ii) is carried out in a distillation column, comprising a reboiler and condenser at a pressure below 500 mbar and with a temperature at the bottom of said distillation column being below 453 K.

* * * * *